United States Patent
Sarabia et al.

(10) Patent No.: US 11,103,276 B2
(45) Date of Patent: Aug. 31, 2021

(54) DUAL LUMEN DILATOR FOR USE IN TRANSSEPTAL PUNCTURES

(71) Applicants: Jaime Eduardo Sarabia, Mableton, GA (US); David Scott Lim, Keswick, VA (US)

(72) Inventors: Jaime Eduardo Sarabia, Mableton, GA (US); David Scott Lim, Keswick, VA (US)

(73) Assignee: 510 KARDIAC DEVICES, INC., Mableton, GA (US)

(*) Notice: Subject to any disclaimer, the term of this patent is extended or adjusted under 35 U.S.C. 154(b) by 153 days.

(21) Appl. No.: 15/711,597

(22) Filed: Sep. 21, 2017

(65) Prior Publication Data

US 2018/0116690 A1 May 3, 2018

Related U.S. Application Data

(60) Provisional application No. 62/416,365, filed on Nov. 2, 2016.

(51) Int. Cl.
*A61B 17/34* (2006.01)
*A61M 25/09* (2006.01)
(Continued)

(52) U.S. Cl.
CPC ...... *A61B 17/3401* (2013.01); *A61B 17/0057* (2013.01); *A61B 17/3403* (2013.01); *A61B 17/3478* (2013.01); *A61M 25/003* (2013.01); *A61M 25/0026* (2013.01); *A61M 25/09* (2013.01); *A61B 17/3417* (2013.01); *A61B 2017/00247* (2013.01);
(Continued)

(58) Field of Classification Search
CPC .......... A61M 2025/0037; A61M 2025/09058; A61M 2025/09175; A61M 25/0026
See application file for complete search history.

(56) References Cited

U.S. PATENT DOCUMENTS

| 4,619,643 A | * | 10/1986 | Bai | ................... A61M 5/1582 604/170.03 |
| 2003/0130617 A1 | | 7/2003 | Leone | |

(Continued)

FOREIGN PATENT DOCUMENTS

| WO | 98/48882 A1 | 11/1998 |
| WO | 98/48885 A1 | 11/1998 |

OTHER PUBLICATIONS

International Search Report and Written Opinion for PCT/US2017/053699 dated Nov. 24, 2017.

(Continued)

*Primary Examiner* — Jenna Zhang
(74) *Attorney, Agent, or Firm* — Nelson Mullins Riley & Scarborough LLP

(57) ABSTRACT

A dilator assembly comprising an elongated body having a proximal end and a distal end, a first lumen extending along the body, a second lumen extending along the body so that it is a parallel to the first lumen, and a joint lumen disposed adjacent the distal end of the body, wherein both the first lumen and second lumen are in fluid communication with the joint lumen. A guidewire has a first end and a second end, and the first end of the guidewire is slidably received in the first lumen and the second end of the guidewire is slidably received in the second lumen.

16 Claims, 2 Drawing Sheets

(51) Int. Cl.
  *A61M 25/00* (2006.01)
  *A61B 17/00* (2006.01)
  *A61M 39/10* (2006.01)
  *A61B 17/22* (2006.01)
  *A61B 18/00* (2006.01)
  *A61F 2/24* (2006.01)
  *A61M 29/02* (2006.01)

(52) U.S. Cl.
  CPC ............... *A61B 2017/00292* (2013.01); *A61B 2017/22042* (2013.01); *A61B 2017/22044* (2013.01); *A61B 2017/22074* (2013.01); *A61B 2017/22077* (2013.01); *A61B 2018/00351* (2013.01); *A61F 2/2427* (2013.01); *A61M 2025/0037* (2013.01); *A61M 2025/0915* (2013.01); *A61M 2025/09116* (2013.01); *A61M 2025/09133* (2013.01); *A61M 2025/09175* (2013.01); *A61M 2029/025* (2013.01); *A61M 2039/1083* (2013.01); *A61M 2039/1088* (2013.01)

(56) References Cited

U.S. PATENT DOCUMENTS

| | | | |
|---|---|---|---|
| 2004/0073141 A1* | 4/2004 | Hartley | A61M 25/09033 600/585 |
| 2006/0253088 A1* | 11/2006 | Chow | A61M 25/003 604/284 |
| 2008/0114303 A1 | 5/2008 | Tremaglio | |
| 2009/0112153 A1 | 4/2009 | Gregersen et al. | |
| 2012/0035590 A1* | 2/2012 | Whiting | A61B 17/3468 604/528 |
| 2015/0127032 A1* | 5/2015 | Lentz | A61B 17/320708 606/159 |
| 2016/0175009 A1* | 6/2016 | Davies | A61B 90/39 606/47 |
| 2019/0167305 A1* | 6/2019 | Pedersen | A61M 25/09 |

OTHER PUBLICATIONS

International Preliminary Report on Patentability for PCT/US2017/053699 dated May 7, 2019.
Supplementary European Search Report completed Apr. 21, 2020 for Application No. EP 17868275.

* cited by examiner

DUAL LUMEN DILATOR FOR USE IN TRANSSEPTAL PUNCTURES

CLAIM OF PRIORITY

This application claims priority to U.S. Provisional Application No. 62/416,365, filed Nov. 2, 2016, the entire disclosure of which is incorporated by reference herein.

FIELD OF THE INVENTION

The present disclosure relates generally to medical devices and, more specifically, to trocars and dilators/obturators.

BACKGROUND

Increasingly, minimally-invasive, catheter-based therapies are being developed that allow physicians to provide therapies to patients whose existing comorbidities may preclude them from having a needed, but more invasive, surgical procedure. Over the last 30-plus years, catheter based procedures that involve puncturing/crossing the interatrial septum, such as cardiac ablation and balloon valvuloplasty have become commonplace. In the last 5 to 10 years, new structural heart procedures, such as transcatheter valve repair/replacement, and left atrial appendage occlusion, have gained regulatory approvals and have become increasingly common procedures performed in the cardiac catheterization laboratory or hybrid operating room. With the advent of these technologies has come an increase in the need for structural heart interventionalists (specialty physicians who perform these types of procedures) to engage and cross the interatrial septum in the heart.

Historically, crossing the septum has been the purview of pediatric cardiologists or electrophysiologists due to the prevalence of cardiac ablation procedures which require crossing the interatrial septum. However, interventional cardiologists are increasingly starting to provide therapy to the left side of the heart and the requirement to puncture the ineteratrial septum and provide these new therapies is increasing. Unfortunately, many of these interventional cardiologists do not perform a transseptal puncture with enough regularity to become proficient at it. For these left-sided procedures, safely puncturing the interatrial septum and gaining access to the left side of the heart is not enough. These new technologies demand a very specific and safe location when crossing the interatrial septum. Additionally, crossing the interatrial septum has been historically guided by fluoroscopy (X-ray), and more recently by echocardiographic ultrasound (intracardiac echocardiography, transephogeal echocardiography or transthoracic echocardiography). Fluoroscopy is limited in its role due to its limited ability to image soft tissue, such as the interatrial septum. Therefore, echocardiography is increasingly being relied upon to guide these types of procedures.

As such, it is desirable to provide these newly evolving structural heart interventionalists with a tool to help them safely and accurately cross the interatrial septum. For example, it is desirable to have a tool this is configured to be used in conjunction with a steerable sheath to permit the use of a back end of a standard guidewire to puncture the interatrial septum rather than using a needle. A double lumen design will help prevent the need to use multiple needles/guidewires as a single guidewire may now perform all the necessary functions.

The present invention recognizes and addresses considerations of prior art constructions and methods.

SUMMARY

One embodiment of a dilator assembly in accordance with the present disclosure includes an elongated body having a proximal end and distal end, a first lumen extending along the body, a second lumen extending along the body so that it is a parallel to the first lumen, and a joint lumen disposed adjacent the distal end of the body, wherein both the first lumen and second lumen are in fluid communication with the joint lumen. A guidewire has first end and second end, and the first end of the guidewire is slidably received in the first lumen and the second lumen end of the guidewire is slidably received in the second lumen.

Another embodiment of a dilator assembly for use with a guidewire having a first end and a second end, include; an elongated body having a proximal end and distal end, a first lumen extending along the body, a second lumen extending along the body so that it is a parallel to the first lumen, and a joint lumen disposed adjacent the distal end of the body, wherein both the first lumen and second lumen in fluid communication with the joint lumen. A first luer has a first luer line that is fluid communication with the first lumen, and a second luer has a second luer line that is in fluid communication with the second lumen, wherein the first end of the guidewire is slidably received in both the first luer line and the first lumen and the second end of the guidewire is slidably received in both the second luer line and the second lumen.

Another embodiment of an introducer sheath assembly in accordance with the present disclosure includes a handle portion with a front end and a rear end, a introducer sheath extending outwardly from the front end of the handle portion, the introducer sheath including a device lumen configured to slidably receive a corresponding device, and a device locking assembly disposed at the rear end of the housing portion, including an elongated stem defining an axially extending bore that is confirmed to slidably receive the corresponding device, the elongated stem being axially movable with respect to the handle portion, a clamp disposed on the distal end of the elongated stem, the clamp being positionable between a locked position in which the corresponding device is axially fixed with respect to the elongated stem and an un-locked position in which the corresponding device is slidable within the axially extending bore of the elongated stem.

BRIEF DESCRIPTION OF THE DRAWINGS

The accompanying drawings, which are incorporated in and constitute a part of this specification, illustrate one or more embodiments of the invention and, together with the description, serve to explain the principles of the invention.

A full and enabling disclosure of the present invention, including the best mode thereof, directed to one of ordinary skill in the art, is set forth in the specification, which makes reference to the appended drawings, in which.

Figure 1:
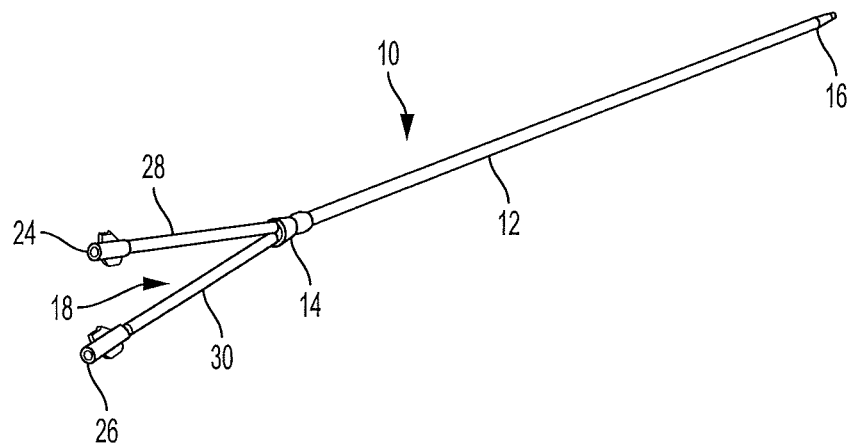
FIG. 1 is a perspective view of a dual lumen dilator assembly in accordance with an embodiment of the present disclosure.

Repeat use of reference characters in the present specification and drawings is intended to represent same or analogous features or elements of the invention according to the disclosure.

DETAILED DESCRIPTION OF THE PREFERRED EMBODIMENTS

Reference will now be made in detail to presently preferred embodiments of the invention, one or more examples of which are illustrated in the accompanying drawings. Each example is provided by way of explanation, not limitation, of the invention. In fact, it will be apparent to those skilled in the art that modifications and variations can be made in the present invention without departing from the scope and spirit thereof. For instance, features illustrated or described as part of one embodiment may be used on another embodiment to yield a still further embodiment. Thus, it is intended that the present invention covers such modifications and variations as come within the scope of the appended claims and their equivalents. As well, directions given for deflection of the distal portion of the introducer sheath of the present invention are given as left or right of a vertical plane that passes through longitudinal center axis 102 (FIG. 1) of the disclosed introducer sheath assembly, when the introducer sheath is fully extended. Note, the introducer sheath assembly is, preferably, substantially symmetrical about the vertical plane.

Figure 2:
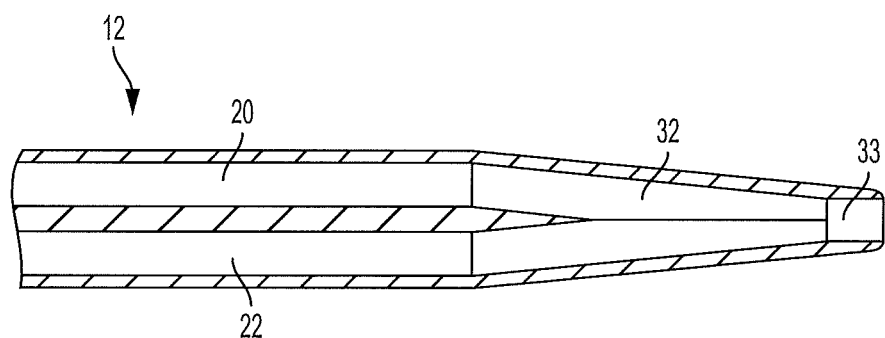
FIG. 2 is a partial, cross-sectional view of a distal end of the dilator assembly shown in FIG. 1, showing the two lumens combining into a simple lumen.
Figure 3:
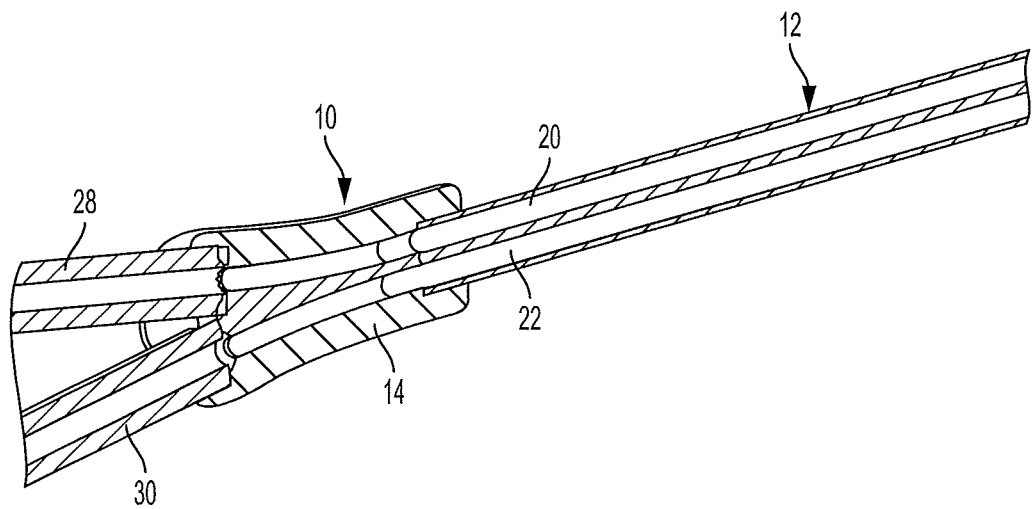
FIG. 3 is a partial perspective view of a central hub of the dilator assembly shown in FIG. 1, which shows details of how the two independent lumens are attached to the central hub so that they may extend along a body of the dilator assembly in parallel fashion.

Referring now to FIGS. 1 through 3, a dual lumen dilator assembly 10 in accordance with an embodiment of the present disclosure includes an elongated body portion, a central hub 14, and first and second luer lines 28 and 30, having first and second luers 24 and 26, respectively. As been seen in FIG. 3, elongated body 12 extends outwardly from a first end of central hub 14, and a first lumen and a second lumen 20 and 22, respectively, extend along body 12 from central hub 14 to a tapered distal end 16 of body 12. First and second lumens 20 and 22 are parallel to each other and remain separated from each other until coming together at joint lumen 32, ultimately forming a single exit lumen 33, which is preferably at the distal end 16 of elongated body 12. Note, however, first and second lumens 20 and 22 may come together to form the joint lumen at other positions along elongated body 12.

Referring specifically to FIG. 2, an enlarged, cross-sectional view of distal end 16 of elongated body 12 is shown. As shown, first and second lumens 20 and 22 are parallel to each other along body 12, but combine at a joint lumen portion 32 to form a single exit lumen 33 at distal end 16 of the assembly. The integration of first and second lumens 20 and 22 may be from an the extrusion or may be separate components that are manufactured independently and then joined to the extrusion for the purpose of uniting the two lumens. The geometry of joint lumen portion 32 is designed in such a manner that regardless of guidewire 34 (FIGS. 4 and 5) advancement or retraction, guidewire 34 successfully finds a lumen through which it can transverse.

Referring now to FIG. 3, a magnified and sectional view of the central hub 14 is shown. The central hub 14 diverts first and second lumens 20 and 22 from elongated body 12 of the dilator assembly away from each other and couples each lumen of the assembly to a corresponding one of luer lines 28 and 30.

Figure 4:
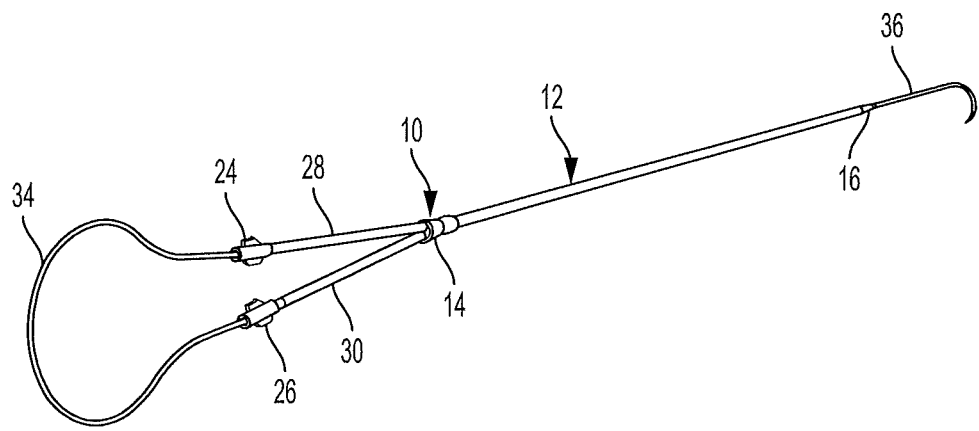
FIG. 4 is a perspective view of the dilator assembly shown in FIG. 1, wherein a floppy distal end of a corresponding guidewire extends outwardly from the distal end of the dilator assembly.
Figure 5:
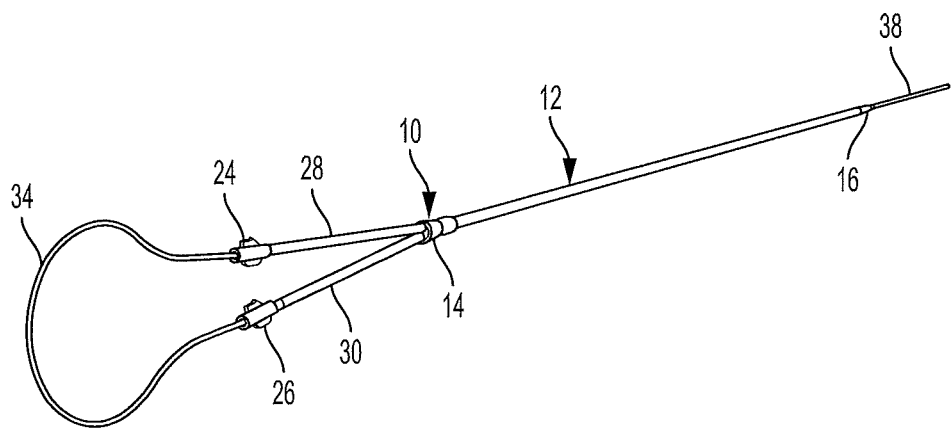
FIG. 5 is a perspective view of the dilator assembly shown in FIG. 1, wherein a stiff end of the corresponding guidewire extends outwardly from the distal end of the dilator assembly.

Referring now to FIG. 4, a perspective view of dilator assembly 10 is shown with a guidewire 34 inserted in a first configuration. In the first configuration, a floppy, distal (front) end 36 of guidewire 34 extends outwardly from distal end 16 of body 12, as discussed in greater detail below. Referring to FIG. 5, a perspective view of dilator assembly 10 is shown with guidewire 34 inserted in a second configuration. In the second configuration, a straight, rigid proximal (back) end of guidewire 34 extends outwardly from distal end 16 and elongated body 12, as discussed in greater details below.

As noted above, dilator assembly 10 preferably includes two lumens 20 and 22 running along most of the length of the body of dilator assembly. The first and second lumens 20 and 22 combine at joint lumen portion 32 somewhere along the length of the dilator (preferably towards the distal end of the elongated body of the dilator assembly) to form a single exit lumen 33. This configuration of dilator assembly 10 allows a physician to track the dilator/sheath assembly over a previously placed guidewire 34 (FIG. 4), as is the normal practice. Once the desired location of their transseptal dilator assembly system is attained, the proximal (back) end 38 of the guidewire is inserted into the second, open lumen 22 by way of second luer 26 and second luer line 30 and advanced towards distal end 16 of body 12. The floppy, distal (front) end 36 of the guidewire is then retracted, which opens up the exit lumen 33 for advance of the stiff, proximal (back) end 38 of the guidewire. The stiff back end 38 of the guidewire is then used to puncture the interatrial septum. Upon puncturing the septum, the stiff back end 38 of the guidewire is retracted, the dilator assembly 10 is advanced into the left atrium, and then the floppy front end 36 of the guidewire is re-advanced into the left atrial via exit lumen 33, thus providing safe, guidewire access into the left atrium. These operations occur without requiring the removal or reinsertion of multiple guidewires and needles, thus increasing the efficiency and safety of transseptal punctures.

Dilator assembly 10 negates the need to use a separate needle to puncture the interatrial septum and, therefore, provides time savings as it eliminates the need for device exchanges. When the floppy, distal end 36 of the guidewire is needed for dilator assembly advancement and tracking, it is extended out of the distal end of the dilator assembly's body and tracked over as needed for the advancement of the dilator assembly. Once the functionality of tracking and advancement is no longer required, distal end 36 end of the guidewire is retracted within body 12 of dilator assembly 10 and the more rigid proximal end 38 of the guidewire is used for puncture. These two features of the guidewire are used interchangeably and rapidly as needed.

While one or more preferred embodiments of the invention are described above, it should be appreciated by those skilled in the art that various modifications and variations can be made in the present invention without departing from the scope and spirit thereof. It is intended that the present invention cover such modifications and variations as come within the scope and spirit of the appended claims and their equivalents.

What is claimed:

1. A dilator assembly comprising:
   an elongated body having a proximal end and a distal end, a first lumen extending along the body, a second lumen extending along the body so that it is parallel to the first lumen, and a joint lumen disposed adjacent the distal end of the body, wherein both the first lumen and second lumen are in fluid communication with the joint lumen; and
   a guidewire having a first end, a second end, and a body portion extending therebetween, wherein the second end of the guidewire is more rigid than the first end of the guidewire such that the second end of the guidewire is adapted to puncture an interatrial septum during a procedure,
   wherein the first end of the guidewire is slidably received in the first lumen and the second end of the guidewire is slidably received in the second lumen so that the first and the second ends of the guidewire are proximate the distal end of the elongated body and the body portion of the guidewire is proximate the proximal end of the elongated body.

2. The dilator assembly of claim 1, further comprising:
   a first luer having a first luer line that is fluid communication with the first lumen; and
   a second luer having a second luer line that is in fluid communication with the second lumen.

3. The dilator assembly of claim 2, further comprising:
   a central hub, wherein the elongated body extends outwardly from a first end of the central hub and the first and the second luer lines extend outwardly from a second end of the central hub.

4. The dilator assembly of claim 2, wherein the distal end of the elongated body includes a tapered end.

5. The dilator assembly of claim 4, wherein the tapered end of the elongated body is defined by an outer frustoconical surface.

6. A dilator assembly comprising:
   an elongated body having a proximal end and a distal end, a first lumen extending along the body, a second lumen extending along the body so that it is parallel to the first lumen, and a joint lumen disposed adjacent the distal end of the body, wherein both the first lumen and second lumen in fluid communication with the joint lumen;
   a guidewire having a first end, a second end, and a body portion extending therebetween, wherein the second end of the guidewire is more rigid than the first end of the guidewire such that the second end of the guidewire is adapted to puncture an interatrial septum during a procedure;
   a first luer having a first luer line that is in fluid communication with the first lumen; and
   a second luer having a second luer line that is in fluid communication with the second lumen;
   wherein the first end of the guidewire and the second end of the guidewire are disposed adjacent the distal end of the elongated body, and the body portion of the guidewire is adjacent the proximal end of the elongated body.

7. The dilator assembly of claim 6, further comprising:
   a central hub, wherein the elongated body extends outwardly from a first end of the central hub and the first and second luer lines extent outwardly from a second end of the central hub.

8. The dilator assembly of claim 6, wherein the distal end of the elongated body includes a tapered end.

9. The dilator assembly of claim 8, wherein the tapered end of the elongated body is defined by an outer frustoconical surface.

10. A dilator assembly comprising:
    an elongated body having a proximal end and a distal end, a first lumen extending along the body, a second lumen extending along the body, and a joint lumen disposed adjacent the distal end of the body, wherein both the first lumen and second lumen are in fluid communication with the joint lumen; and
    a guidewire having a first end, a second end, and a body portion extending therebetween, wherein the second end of the guidewire is more rigid than the first end of the guidewire such that the second end of the guidewire is adapted to puncture an interatrial septum during a procedure,
    wherein the first end of the guidewire is slidably received in the first lumen and the second end of the guidewire is slidably received in the second lumen, and the joint lumen is sized so that only one of the first end and the second end of the guidewire is extendable therethrough at a time.

11. The dilator assembly of claim 10, wherein the first and the second ends of the guidewire are proximate the distal end of the elongated body and the body portion of the guidewire is proximate the proximal end of the elongated body.

12. The dilator assembly of claim 10, further comprising:
    a first luer having a first luer line that is fluid communication with the first lumen; and
    a second luer having a second luer line that is in fluid communication with the second lumen.

13. The dilator assembly of claim 12, further comprising:
    a central hub, wherein the elongated body extends outwardly from a first end of the central hub and the first and the second luer lines extend outwardly from a second end of the central hub.

14. The dilator assembly of claim 12, wherein the distal end of the elongated body includes a tapered end.

15. The dilator assembly of claim 14, wherein the tapered end of the elongated body is defined by an outer frustoconical surface.

16. The dilator assembly of claim 11, wherein the first and the second ends of the guidewire are disposed inside the distal end of the elongated body.

* * * * *

UNITED STATES PATENT AND TRADEMARK OFFICE
CERTIFICATE OF CORRECTION

| | | |
|---|---|---|
| PATENT NO. | : 11,103,276 B2 | Page 1 of 1 |
| APPLICATION NO. | : 15/711597 | |
| DATED | : August 31, 2021 | |
| INVENTOR(S) | : Jaime Eduardo Sarabia et al. | |

It is certified that error appears in the above-identified patent and that said Letters Patent is hereby corrected as shown below:

On the Title Page
Right column, in item (57) "Abstract", Line 4, delete "it is a parallel to..." and replace with --it is parallel to...--.

In the Specification
In Column 1, Line 42, delete "ineteratrial" and replace with --interatrial--.
In Column 1, Lines 52-53, delete "transephogeal" and replace with --transesophageal--.
In Column 2, Line 10, delete "it is a parallel to..." and replace with --it is parallel to...--.
In Column 2, Line 21, after "is" delete "a".
In Column 2, Line 25, after "is" insert --in--.
In Column 3, Line 63, delete "an the" and insert --an--.

In the Claims
In Column 5, Claim 2, Line 24, after "is" insert --in--.
In Column 6, Claim 12, Line 40, after "is" insert --in--.

Signed and Sealed this
Nineteenth Day of April, 2022

Katherine Kelly Vidal
*Director of the United States Patent and Trademark Office*